United States Patent
Goughnour

[11] Patent Number: 5,906,801
[45] Date of Patent: May 25, 1999

[54] DECONTAMINATION APPARATUS SHELF SYSTEM

[75] Inventor: Jeffrey A. Goughnour, Erie, Pa.

[73] Assignee: Steris Corporation, Mentor, Ohio

[21] Appl. No.: 08/796,720

[22] Filed: Mar. 3, 1997

[51] Int. Cl.[6] ...................................................... A61L 2/00
[52] U.S. Cl. ........................... 422/300; 422/297; 211/194
[58] Field of Search .................................... 422/297, 300, 422/302; 211/49.1, 59.4, 69, 194; 206/202, 501; 220/487; 294/97

[56] References Cited

U.S. PATENT DOCUMENTS

| | | | |
|---|---|---|---|
| 2,512,747 | 6/1950 | Lewis | 422/300 X |
| 2,730,263 | 1/1956 | Neilson . | |
| 5,358,112 | 10/1994 | Gardner | 206/369 |
| 5,384,103 | 1/1995 | Miller | 422/297 X |
| 5,415,846 | 5/1995 | Berry, Jr. | 422/297 |
| 5,433,929 | 7/1995 | Riihimaki et al. | 422/297 |
| 5,451,379 | 9/1995 | Bowlin, Jr. | 422/297 |
| 5,525,314 | 6/1996 | Hurson | 422/297 X |

OTHER PUBLICATIONS

Block, Seymour S. *Disinfection, Sterilization and Preservation*, 3rd ed., pp. 505–505, 1991.
Applicant's Sketch of Schaerer Vapufix 602 Shelf of at least Aug., 1996.

*Primary Examiner*—Elizabeth McKane
*Attorney, Agent, or Firm*—Fay, Sharpe, Beall, Fagan, Minnich & McKee, LLP

[57] ABSTRACT

A decontamination device (10) including a chamber (14) for receiving articles (28 and 30) to be decontaminated by at least one of washing, disinfecting and sterilizing. The decontamination device also includes a shelving assembly (22) for suspending the articles (28 and 30) in the chamber. The shelving assembly (22) is constructed of a first body (26) suspended above the floor of the chamber (14) having a major surface (56) facing the top of the chamber (14). At least two side walls (58 and 60) extend generally upward from the major surface (56). A second body (24) having a major surface (46) facing the floor of the chamber (14) and at least two side walls (48 and 50) is stacked on the first body (26), wherein the two side walls (48 and 50) of the second body (24) mate with the two side walls (58 and 60) of the first body (26), supporting the second body (24).

9 Claims, 3 Drawing Sheets

DECONTAMINATION APPARATUS SHELF SYSTEM

BACKGROUND OF THE INVENTION

The present invention relates generally to the decontamination art. It finds particular application in the washing, sterilizing and disinfecting apparatus typically employed to clean, sterilize and disinfect medical, dental, veterinary, mortuary and laboratory instruments and equipment and will be described with particular reference thereto. It will be appreciated, however, that the invention may be applicable to a wide variety of apparatus used in sanitizing.

Medical, dental, surgical, veterinary and laboratory equipment and instruments are often cleaned, and/or sterilized by water/detergent washing, steam, $H_2O_2$ or other vapor treatments, or reagent treatments. More particularly, an apparatus is provided which isolates the equipment and instruments in these respective environments for a sufficient period of time to complete the cleaning and/or sterilization. Washing apparatus of the type used in institutional settings; the steam autoclave devices of the type described in U.S. Pat. Nos. 4,193,818; 4,226,642; and 4,601,300; the reagent type sterilization devices of the type described in U.S. Pat. Nos. 4,731,222; 5,037,623; and 5,391,360; and the hydrogen peroxide systems of the type described in U.S. Pat. Nos. 4,169,123 and 4,169,124 provide examples of cleaning and decontamination apparatus with which the present invention is particularly suited. Each of these patents is hereby incorporated by reference.

One element often found in each of these devices is a shelving arrangement to support a load of instruments or other equipment (the "load") being cleaned and/or sterilized in the appropriate location within a chamber to achieve the desired results.

A shelving system must accomplish a variety of goals. Particularly, it is desirable that the shelving system provide clearance of the load from the chamber walls. In addition, the shelving system must be sufficiently strong to support the load. However, the mass of the shelving must be kept relatively low to prevent wet pack loads, particularly in steam cleaning, where steam would condense on overly massive shelves. In addition, the shelving system must include sufficient ventilation to allow a cleaning solution, a sterilization solution and/or a vapor to reach the load being decontaminated. Moreover, the shelving system should not interfere with the circulation of these liquids and decrease the effectiveness of the operation.

Historically, a typical rack system has been constructed of a wrapped wire or rod suspended on a tubular support. The tubular support is generally self-suspending on a plurality of support guides permanently secured to the walls of the decontamination chamber. Unfortunately, these systems are typically expensive to manufacture as a result of the significant amount of time required in tube bending and tack welding.

The present invention contemplates a new and improved shelving system which provides the necessary performance yet is easily manufactured at a low cost.

SUMMARY OF THE INVENTION

In accordance with one aspect of the present invention, a decontamination or cleaning device having a chamber for receiving articles to be decontaminated by either washing, disinfecting or sterilizing is provided. The chamber may include a top, a floor, two side walls and front and back walls. For purposes of this disclosure, these walls may be also characterized as quadrants of a spherical chamber, wherein distinct transitions in the form of corners are not present. Often, the top, front, or back wall is formed by a door which provides access to the chamber. In general, the housing is sized appropriately to receive articles to be decontaminated or cleaned. Typically, the articles are positioned in the chamber and suspended on a shelving assembly.

According to the present invention, a shelving assembly is provided that includes a first element which has a major wall facing the top of the chamber and at least two minor side walls extending upwardly from opposed edges of the major wall. A second element of the shelving assembly has a major wall facing the major wall of the first element and at least two minor side walls depending from opposed edges of the major wall. In an assembled form, the side walls of the first element and the side walls of the second element are aligned and mated and provide a spaced relationship between the facing major walls of the first and second elements.

In accordance with a more limited aspect of the invention, the major surfaces of the first and second elements of the shelving assembly are generally co-planar and include a plurality of holes. Preferably, the side walls of at least the top element of the shelving assembly include additional ports.

In accordance with another aspect of the invention, the lower portion of the shelving assembly includes a mating extension which is demountably secured to a bracket fixed to a wall of the chamber. Preferably, in an autoclave, the bracket will also act as a steam baffle within the chamber. In addition, an edge opposed from the mating extension will include a downwardly directed leg which engages a floor of the chamber.

In a further alternative embodiment, each of the side walls of the first and second element of the shelving assembly include laterally extending, co-planar flanges which provide cooperative mating surfaces. In addition, the flanges may include inter-locking slot and key elements to provide a secure and fixed relationship.

A primary advantage of the invention is ease of manufacture. A further advantage of the present invention is provided by the modular nature of the invention. Particularly, a plurality of brackets can be provided on a wall of the chamber to allow a plurality of shelving units to be positioned within the decontamination chamber. Similarly, the invention contemplates the use of a system including a plurality of variously sized upper members allowing for a wide flexibility in accommodating differently sized loads.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

DETAILED DESCRIPTION OF THE INVENTION

Shelves are required inside a sterilization or washing device as a means of supporting a load, typically made up of trays or baskets containing medical equipment or laboratory instruments. The present inventive system is a modular system which provides for vertical stacking inside a chamber. The system includes at least two pieces, a base selectively fixed to the chamber wall and a top unit mounted on the bottom unit, each being removable for cleaning. For large decontamination chambers, the system may include a plurality of stacked units.

Beneficial characteristics of the inventive shelving assembly include clearance between the load(s) and the chamber walls and a material mass of each shelf low enough to prevent wet pack loads. At the same time, each unit is strong enough to support the required load ranges. The bottom rack also has side extensions which help redirect sterilant away from the load.

Figure 1:
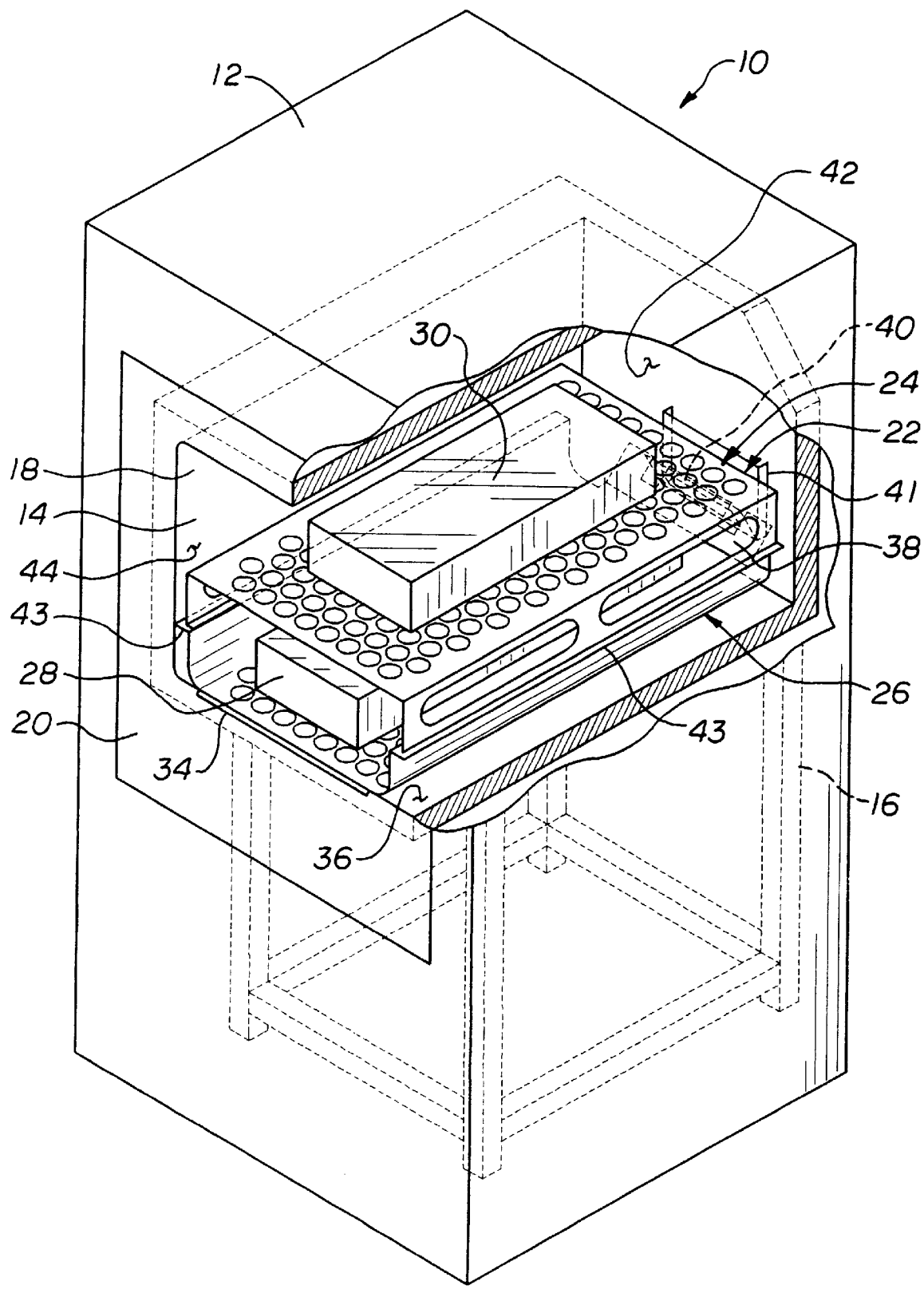
FIG. 1 is a perspective view of a steam sterilization device, partially in cross-section, depicting the inventive shelving assembly.

For convenience of this description, like numbers are used to represent like elements throughout the specification. Referring now to FIG. 1, a steam sterilization apparatus 10 is depicted, however, only those features of a steam sterilization device associated with the present inventive shelving design are shown. Other necessary aspects of the device will be recognized and known to those of ordinary skill in the art.

The steam sterilization device 10 includes an outer housing 12 within which a sterilization chamber 14 is disposed. The chamber 14 is elevated on a stand 16 to locate an open end 18 adjacent an opening 20 in the housing 12 and allows an operator to load equipment into the chamber. A door (not shown) is then used to seal the chamber 14 to provide an appropriate sterilization environment.

Figure 5:
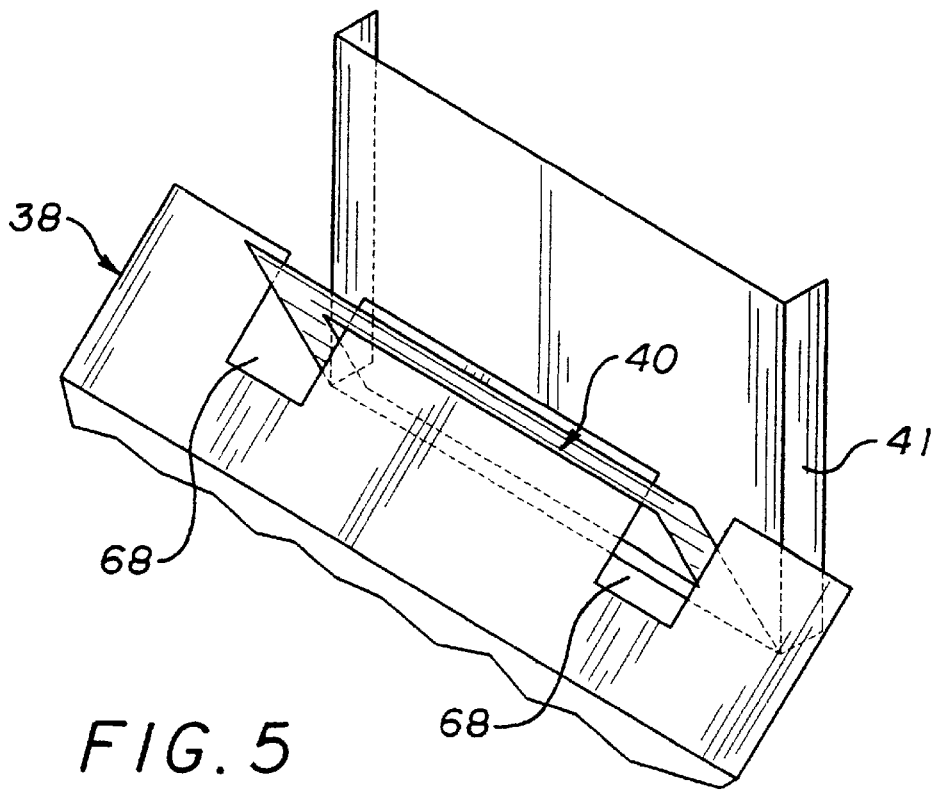
FIG. 5 is a perspective view of the interlocking baffle arrangement between the bottom rack and a baffle secured to the wall of the device chamber.

Disposed within the chamber 14 is a shelving assembly 22. The shelving assembly 22 includes a top rack 24 mated to a bottom rack 26. A first load 28 is supported on the on bottom rack 26 and a second load 30 on the top rack 24. The shelving assembly 22 is supported via a front leg 34 resting on a floor 36 of the chamber 14. The rear edge of shelving assembly 22 includes an interlocking extension member 38 which mates with bracket 40, which in turn, is secured to baffle 41, itself secured to a rear wall 42 of the chamber 14. FIG. 5 provides a more detailed view of the mating arrangement and is described herein-below. However, it is noted that baffle 41 is preferably positioned to cover a steam inlet (not shown) in the rear wall 42. In this regard, steam injected into the chamber 14 is therefore directed upward into a desirable flow pattern by the baffle 41.

In accord with the depicted arrangement, the bottom rack 26 of the shelving assembly 22 is supported above the floor 36 of the chamber 14 allowing appropriate steam flow throughout the unit and avoiding the possibility of significant condensate contacting the load 28. Additional support for the shelving assembly 22 is provided by abutting flanges 43 with a side wall 44 of the chamber 14. More particularly, the use of a resilient material to construct the top and bottom rack allows the width of a shelving unit to be slightly narrower than the chamber diameter, allowing easy insertion. After a load is placed on the assembly, flexing of the assembly brings the flanges into context with the chamber walls, providing support for the structure.

Figure 2:
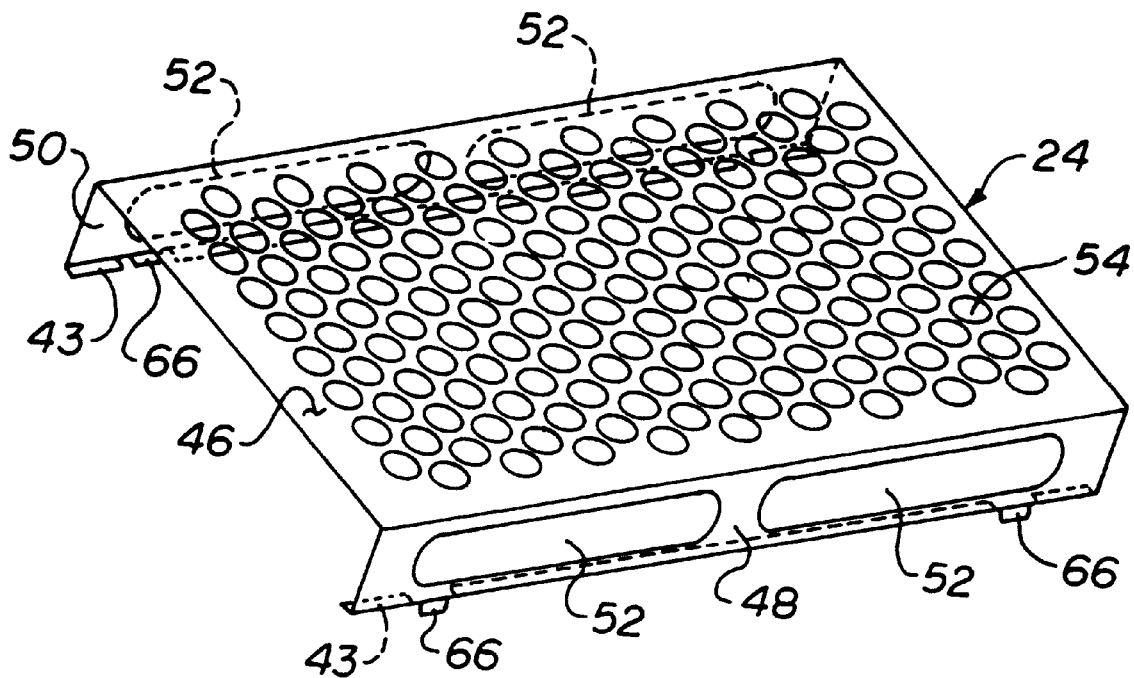
FIG. 2 is a perspective view of the top rack of the shelving assembly.
Figure 3:
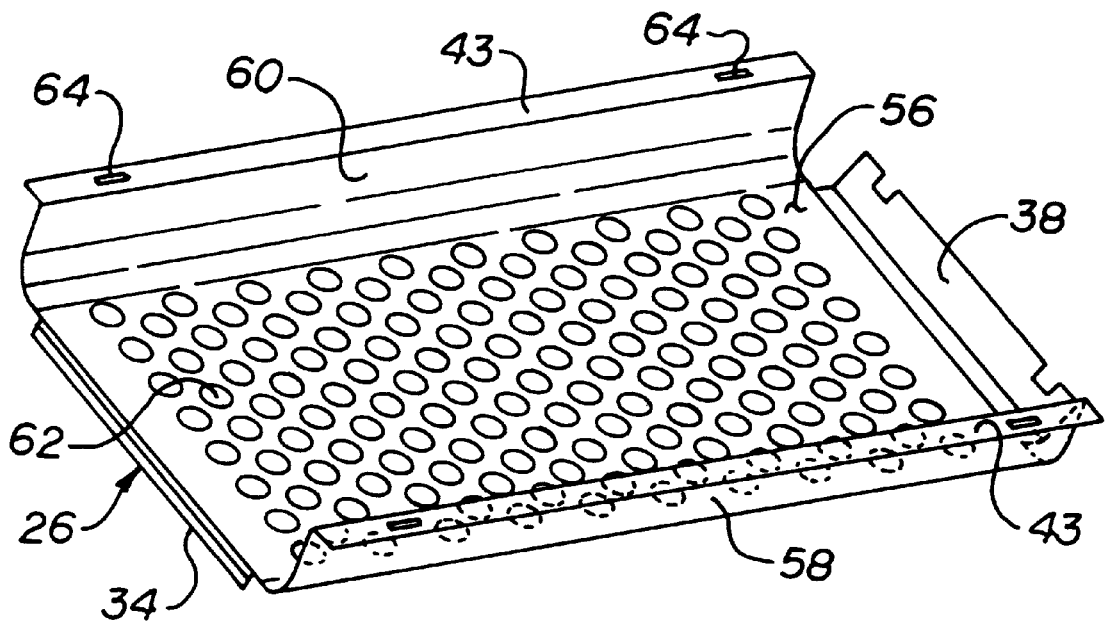
FIG. 3 is a perspective view of the bottom rack of the shelving assembly.
Figure 4:
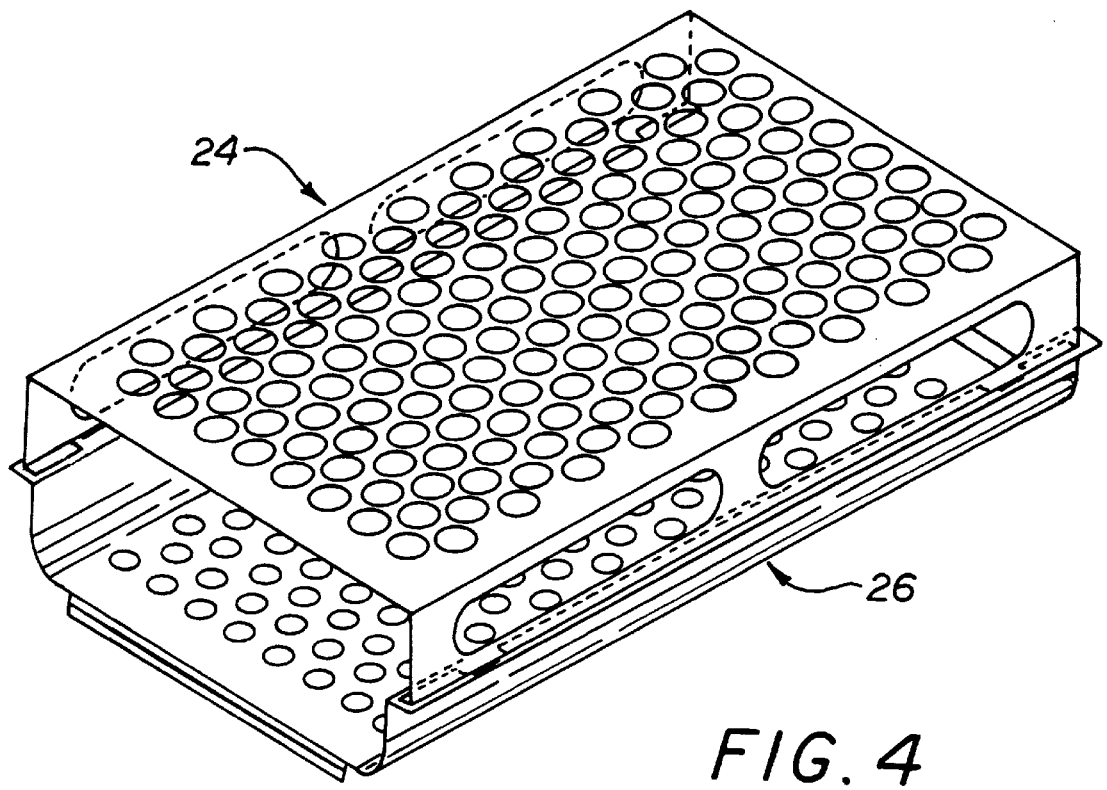
FIG. 4 is a perspective view of the mated top and bottom racks of FIGS. 2 and 3.

Referring now to FIGS. 2, 3 and 4, top rack 24 includes a major planar surface 46 and a pair of downwardly depending sidewalls 48 and 50. Each of the side walls include a pair of large portals 52 which aid sterilant circulation. A plurality of passages 54 are formed in the major planar surface 46 for a similar purpose.

The bottom rack 26 includes a major planar surface 56 and a pair of upwardly extending side walls 58 and 60. A downwardly depending front leg 34 is included and, as depicted in FIG. 1, functions as a front support for the assembly. Extending from a rear edge of the major planar surface 56 is an extension member 38 shaped to interlock with the bracket 40 to support the shelving assembly 22.

Preferably the rack components are comprised of stainless steel. However, any material having sufficient strength and the ability resist formation of condensation within the sterilization chamber may be suited to the present invention. The major surface 56 of bottom unit 26 is constructed to include a plurality of vents 62.

To facilitate a mated relationship between top rack 24 and bottom rack 26, each is constructed to include a flange member 43 extending generally perpendicularly from the side walls 48, 50, 58 and 60. As depicted, the top rack 24 includes inwardly disposed flanges while bottom rack 26 includes outwardly extended flanges, the units being sized to mate the flanges. In addition, the flanges 43 of the lower rack 26 include slots 64 sized to accommodate the protrusions 66 extending from the flanges of top rack 24. This mated relationship is best exemplified in FIG. 4.

Referring now to FIG. 5, the relationship between the support structure in relationship to the baffle 41 and the extension of member 38 is depicted. Moreover, the baffle 41 includes abstract 40 sized to mate with a pair of notches 68 in extension member 38. Removal of the bottom rack is accomplished by lifting the front of the unit to disengage the notches 68 from the bracket 40.

The present invention provides easy adjustment of load capabilities. Lifting and sliding out a top unit can in fact provide for large load capability on only the bottom unit. Furthermore, both racks are easily removable without tools for cleaning purposes. Most importantly, the single piece construction allows for a low cost production of the unit.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A shelving assembly for a front loading decontamination unit, the shelving unit assembly comprising:
   a top piece having a generally elongated planar surface on which articles or cassettes are slidably received for decontamination, two downwardly extending side walls on opposed edges of said planar surface and at least one open end, a plurality of holes being formed in said planar surface, a flange extending generally perpendicular from each said side walls along an edge opposed form said planar surface,
   a bottom piece having a generally elongated planar surface on which articles or cassettes are slidably received for decontamination, a plurality of holes being formed in said planar surface, two upwardly extending side walls along opposed edges, and a flange extending generally perpendicular from each said side walls along an edge opposed from said planar surface, the flanges on said top piece mating with the flanges on said bottom piece to form an enclosure having top, bottom and side walls and at least one open end said top piece being selectively separable from said bottom piece, said bottom piece including an element extending from a rear edge of said planar surface for supporting said shelving unit and removably mating with a bracket and preventing said shelving assembly from sliding with the articles or cassettes a they are slidingly removed.

2. The shelving of claim 1 being comprised of stainless steel.

3. The shelving of claim 1 including a plurality of vents in the side walls of said top piece.

4. The shelving of claim 1 wherein said bottom piece includes at least one depending leg.

5. The shelving of claim 1 further including a slot or key on said flanges of said top piece and a corresponding slot or key on said flanges of said bottom piece.

6. The shelving assembly of claim 1 further including a depending leg on said bottom piece distally located from a point mating with said bracket and in contact with a floor wall of said decontamination unit.

7. A shelving assembly for a decontamination unit comprising:

a top piece having a generally elongated planar surface, two downwardly extending side walls on opposed edges of said planar surface and at least one open end, a plurality of holes being formed in said planar surface, a supporting surface extending generally perpendicular to said side walls along an edge opposed from said planar surface, a bottom piece having a generally elongated planar surface, a plurality of holes being formed in said planar surface, two upwardly extending side walls along opposed edges, and a supporting surface extending generally perpendicular from said side walls along an edge opposed to said planar surface, the supporting surfaces on said top piece mating with the supporting surfaces on said bottom piece to form an enclosure having top, bottom and side walls and at least one open end, said bottom piece including, a notched plate extending upwardly from an edge of said planar surface to mate with a bracket.

8. The shelving assembly of claim 7 further including a baffle supporting said bracket and extending from a wall of said chamber to redirect a sterilant.

9. The shelving assembly of claim 7 further including a depending leg on said bottom piece distally located from a point of mating with said bracket and in contact with a floor wall of said decontamination unit.

* * * * *